US00PP19588P3

(12) United States Plant Patent
Zaiger et al.

(10) Patent No.: US PP19,588 P3
(45) Date of Patent: Dec. 23, 2008

(54) NECTARINE TREE NAMED 'RED RYAN'

(50) Latin Name: ***Prunus persica* var. *nucipersica***
Varietal Denomination: Red Ryan

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 0 days.

(21) Appl. No.: 11/652,453

(22) Filed: Jan. 12, 2007

(65) Prior Publication Data

US 2008/0184406 P1 Jul. 31, 2008

(51) Int. Cl.
*A01H 5/00* (2006.01)

(52) U.S. Cl. ..... Plt./190

(58) Field of Classification Search ..... Plt./190
See application file for complete search history.

*Primary Examiner*—Annette H Para
*Assistant Examiner*—June Hwu

(57) ABSTRACT

A new and distinct variety of nectarine tree. The following features of the tree and its fruit are characterized with the tree budded on 'Nemagaurd' Rootstock (non-patented), grown on Handford sandy loam soil with Storie Index rating 95, in USDA Hardiness Zone 9, near Modesto, California, with standard commercial fruit growing practices, such as pruning, thinning, spraying, irrigation and fertilization. Its novelty consist of the following combination of desirable features:

1. Fruit ripening in the early maturity season.
2. Fruit with a high degree of attractive red skin color.
3. Heavy and regular production of large size fruit.
4. Having a low winter chilling requirement of approximately 300 hours at or below 45° F.
5. Vigorous and upright growth of tree.
6. Fruit with good flavor and eating quality.

1 Drawing Sheet

Botanical description: *Prunus persica* var. *nucipersica.*

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of nectarine tree was originated and asexually reproduced by us in our experimental orchard located near Modesto, Stanislaus County, Calif.

PRIOR VARIETIES

Among the existing varieties of nectarine trees, which are known to us, and mentioned herein, 'Red Roy' Nectarine (U.S. Plant Pat. No. 12,057), 'Royal Glo' Nectarine (U.S. Plant Pat. No. 8,281), 'Ruby Gold' Nectarine (U.S. Plant Pat. No. 3,101) and 'May Glo' Nectarine (U.S. Plant Pat. No. 5,245).

ORIGIN OF THE VARIETY

The new and distinct variety of nectarine tree (*Prunus persica* var. *nucipersica*) was developed by us in our experimental ochard located near Modesto, Calif. as a first generation cross between 'Red Roy' Nectarine (U.S. Plant Pat. No. 12,057) and a proprietary seedling with the field identification number '202LF602'. The paternal parent (202LF602) originated from crosses between the following varieties; 'Royal Glo' Nectarine (U.S. Plant Pat. No. 8,281), 'May Glo' Nectarine (U.S. Plant Pat. No. 5,245), 'Ruby Gold'

Nectarine (U.S. Plant Pat. No. 3,101) and a nectarine of unknown parentage. A large number of these first generation seedlings were grown and budded to older trees of 'Nemagaurd' Rootstock (non-patented), to accelerate rapid fruit production for evaluation. Under close and careful observation we recognized the desirable fruit characteristics of the present new variety and selected it in 1997 for further asexual propagation and commercialization.

ASEXUAL REPRODUCTION OF THE VARIETY

Asexual reproduction of the new and distinct variety of nectarine tree was by budding to 'Nemagaurd' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new variety of nectarine tree (*Prunus persica* var. *nucipersica*) is of large size, vigorous, upright growth, a productive and regular bearer of large size, firm, yellow flesh, clingstone fruit with good flavor and eating quality. The tree has a low winter chilling requirement of approximately 300 hours at or below 45° F. The fruit is further characterized by ripening in the early maturity season and having a high degree of attractive red skin color. In comparison to its maternal parent 'Red Roy' Nectarine (U.S. Plant Pat. No. 12,057), the tree of the new variety requires approximately 50 hours less winter chilling and the fruit is approximately one week earlier in maturity. In comparison to its pollen parent (202LF602) the tree of the new variety has fruit that is larger in size and matures approximately 5 days earlier. In comparison to 'Royal Glo' Nectarine (U.S. Plant Pat. No. 8,281), the tree of the new variety requires approximately 150 hours less winter chilling and the fruit has a higher degree of attractive red skin color.

PHOTOGRAPH OF THE VARIETY

The accompanying color photographic illustration shows typical specimens of the foliage and fruit of the present new nectarine variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of nectarine tree, its flowers, foliage and fruit, as based on observations of 8 year old specimens grown near Modesto, Calif., with color in accordance with Munsell Book of Color.

Tree:

*Size.*—Large, usually pruned to 3 to 3.5 meters in height and width for economical harvesting of fruit. Size varies with different cultural practices.

*Vigor.*—Vigorous, growth of 1.5 to 2 meters the first growing season. Varies slightly with type and fertility of soil and climatic conditions, and cultural practices.

Form. —Upright, usually pruned to vase shape.

*Branching habit.*—Upright, crotch angle approximately 35° increases with heavy crop load.

*Productivity.*—Productive, normal fruit thinning necessary for desirable market size fruit. Fruit set varies with climatic conditions during bloom season.

*Bearer.*—Regular, adequate fruit set 6 consecutive years.

*Fertility.*—Self-fertile.

*Density.*—Medium dense, pruning to open center of the tree to vase shape desirable to enhance fruit color and keep fruit wood healthy in center of tree.

*Hardiness.*—Hardy in all stone fruit growing areas of California. Tree grown in USDA Hardiness Zone 9. Winter chilling requirement approximately 300 hours at or below 45° F.

Trunk:

*Size.*—Large, circumference of 50.8 cm at 30.6 cm above the ground on a 8 year old tree.

*Stock.*—Medium stocky.

*Texture.*—Medium shaggy, roughness increases with age of tree.

*Color.*—Varies from 5YR 4/2 to SYR 3/2.

Branches:

*Size.*—Medium. Average circumference 20.3 cm at 1.3 meters above ground. Crotch angle approximately 35°, increases with crop load.

*Surface texture.*—New growth relatively smooth. Mature growth medium rough, roughness increases with age.

*Lenticels.*—Average 23 in a 25.8 sq cm area. Average length 2.0 mm. Average width 1.5 mm. Color varies from 7.5YR 7/6 to 7.5YR 6/8.

*Colors.*—New growth varies from 2.5GY 5/6 to 2.5GY 8/6. Old growth varies from 7.5YR 5/6 to 7.5YR 5/8, varies with age of growth.

Leaves:

*Size.*—Medium to large. Average length 130.8 mm. Average width 32.9 mm.

*Form.*—Lanceolate.

*Apex.*—Acuminate.

*Base.*—Cuneate.

*Margin.*—Crenate.

*Thickness.*—Medium.

*Surface Texture.*—Upper surface relatively smooth, slightly indented over midrib and leaf veins. Lower surface relatively smooth except for ridges caused by midrib and pinnate venation. Both surfaces glabrous.

*Petiole.*—Average length 9.8 mm. Average width 1.3 mm. Surface glabrous. Longitudinally grooved. Color varies from 2.5GY 7/8 to 10Y 7/8.

*Stipules.*—None observed on mature leaves.

*Glands.*—Reniform. Size — large. Average length 1.1 mm. Average diameter 0.7 mm. Number varies from 1 to 3, average 2. Located primarily on base of leaf blade and upper portion of petiole. Color varies from 2.5GY 6/6 to 2.5GY 7/6.

*Color.*—Upper surface varies from 2.5GY 4/4 to 2.5GY 4/6. Lower surface varies from 5GY 6/4 to 5GY 5/4. Midvein color varies from 2.5GY 7/6 to 2.5GY 8/6.

Flower buds:

*Size.*—Large. Average length 16.1 mm. Average diameter 8.5 mm.

*Hardiness.*—Hardy with respect to California winters.

*Form.*—Conical, becoming elongated before opening.

*Pedicel.*—Average length 3.0 mm. Average width 1.0 mm. Color varies from 10Y 7/6 to 10Y 6/6.

*Color.*—Varies from 5RP 8/4 to 5RP 8/6.

Flowers:

*Blooming period.*—Date of First Bloom Feb. 8, 2005. Date of Petal Fall Feb. 15, 2005, varies with climatic conditions.

*Size.*—Large, showy. Average height 21.7 mm. Average diameter 31.5 mm.

*Petals.*—Number 5, alternately arranged to sepals. Form — nearly globose. Average length 16.5 mm. Average width 12.0 mm. Margin varies from smooth to slightly scalloped. Color varies from 5RP 8/4 to 5RP 8/6, fades with age of flower.

*Sepals.*—Number 5, alternately arranged to petals. Shape — ovate, apex rounded. Margin — entire. Average length 5.6 mm. Average width 4.1 mm. Upper surface glabrous, lower surface pubescent. Color — upper surface varies from 2.5GY 7/6 to 2.5GY 7/8. Lower surface varies from 2.5R 4/4 to 2.5R 4/8.

*Stamens.*—Average number per flower 42. Average filament length 12.1 mm. Filament color varies from N 9.5/ (white) to 2.5RP 9/2. Anther color varies from 7.5R 3/2 to 7.5R 4/10.

*Pollen.*—Self-fertile. Color varies from 5Y 8.5/6 to 5Y 8/8.

*Pistil.*—Number — normally 1. Surface glabrous. Average length 17.2 mm. Position of stigma relatively even with the anthers. Color varies from 7.5Y 9/4 to 7.5Y 9/6.

*Fragrance.*—Very slight.

*Color.*—Varies from 5RP 8/4 to 5RP 8/6.

*Number flowers per flower bud.*—One.

*Pedicel.*—Average length 3.2 mm. Average width 1.4 mm. Color varies from 2.5GY 7/6 to 2.5GY 7/8.

Fruit:

*Maturity when described.*—Firm ripe.

*Date of first picking.*—May 26, 2005.

*Date of last picking.*—Jun. 1, 2005, varies slightly with climatic conditions.

*Size.*—Large. Average diameter axially 71.4 mm. Average transversely in suture plane 67.7 mm. Average weight 184.6 grams, varies slightly with fertility of the soil, amount of thinning and climatic conditions.

*Form.*—Globose to slightly elongated.

*Suture.*—Nearly smooth to very slightly lipped.

*Ventral surface.*—Rounded to slightly retuse. 9.

*Apex.*—Varies from round to slight point.

*Base.*—Flat to slightly retuse.

Stem:

*Size.*—Medium. Average length 9.3 mm. Average diameter 3.1 mm.

*Cavity.*—Rounded to slightly elongated on suture plane. Average depth 5.2 mm. Average diameter 12.3 mm.

*Color.*—Varies from 10Y 6/8 to 2.5GY 6/8.

Flesh:

*Ripens.*—Relatively even, slightly earlier at apex.

*Texture.*—Firm, meaty.

*Firmness.*—Holds firm on the tree 6 to 7 days after maturity.

*Fibers.*—Few, small, tender.

*Aroma.*—Moderate.

*Amydgalin.*—Undetected.

*Eating quality.*—Good.

*Flavor.*—Good, good balance between sugar and acid.

*Juice.*—Moderate amount, enhances flavor.

*Brix.*—Average Brix 10°, varies slightly with amount of fruit per tree and climatic conditions.

*Stone cavity.*—Shape — obovoid to globose. Average length 37.9 mm. Average width 29.2 mm. Average depth 11.5 mm.

*Color.*—Varies from 2.5Y 8/6 to 2.5Y 8/8. Pit cavity varies from 2.5Y 7/6 to 2.5Y 7/10.

Skin:

*Thickness.*—Medium.

*Surface.*—Smooth.

*Down.*—Wanting.

*Tendency to crack.*—None.

*Color.*—Ground color varies from 2.5Y 8/8 to 2.5Y 8.5/8, overspread with 7.5R 4/14 to 7.5R 3/12.

*Tenacity.*—Tenacious to flesh.

*Astringency.*—None.

Stone:

*Type.*—Clingstone.

*Size.*—Large. Average length 37.3 mm. Average width 29.0 mm. Average thickness 22.3 mm.

*Form.*—Obovoid.

*Base.*—Usually flat, varies from flat to slightly rounded.

*Apex.*—Varies from round to slightly pointed. Average length 0.5 mm.

*Surface.*—Pitted throughout, pits vary from rounded to slightly elongated. Ridges extending from base toward apex.

*Sides.*—Unequal, one side extending further from suture plane.

*Ridges.*—Numerous small ridges extending from base toward apex, relatively smooth.

*Tendency to split.*—Slight.

*Color.*—Varies from 7.5YR 7/6 to 7.5YR 4/8 when dry.

Kernal:

*Form.*—Ovate.

*Taste.*—Bitter.

*Viability.*—Poor, embryo only partially developed.

*Size.*—Medium. Average length 17.9 mm. Average width 11.2 mm. Average depth 6.1 mm.

*Skin.*—Color varies from 2.5Y 9/4 to 2.5Y 8.5/4 when dry.

Use: Dessert. Market — local and long distance.

Keeping quality: Good, held firm in cold storage at 38° to 42° F. for 2 weeks without internal breakdown or appreciable loss of flavor.

Shipping quality: Good, minimal skin scarring or bruising of flesh during picking and packing trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant fruit disease resistance or susceptibility has been observed. Any variety or selection observed during indexing of plant characteristics with abnormal fungus, bacterial, virus or insect susceptibility is destroyed and eliminated from our breeding program.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of nectarine tree, substantially as illustrated and described, characterized by its large size, vigorous, upright growth, with a low winter chilling requirement of approximately 300 hours at or below 45° F., being a regular and productive bearer of large size, yellow flesh clingstone fruit with good flavor and eating quality; the fruit is further characterized by its attractive red skin color, firm flesh, with good handling and shipping qualities.

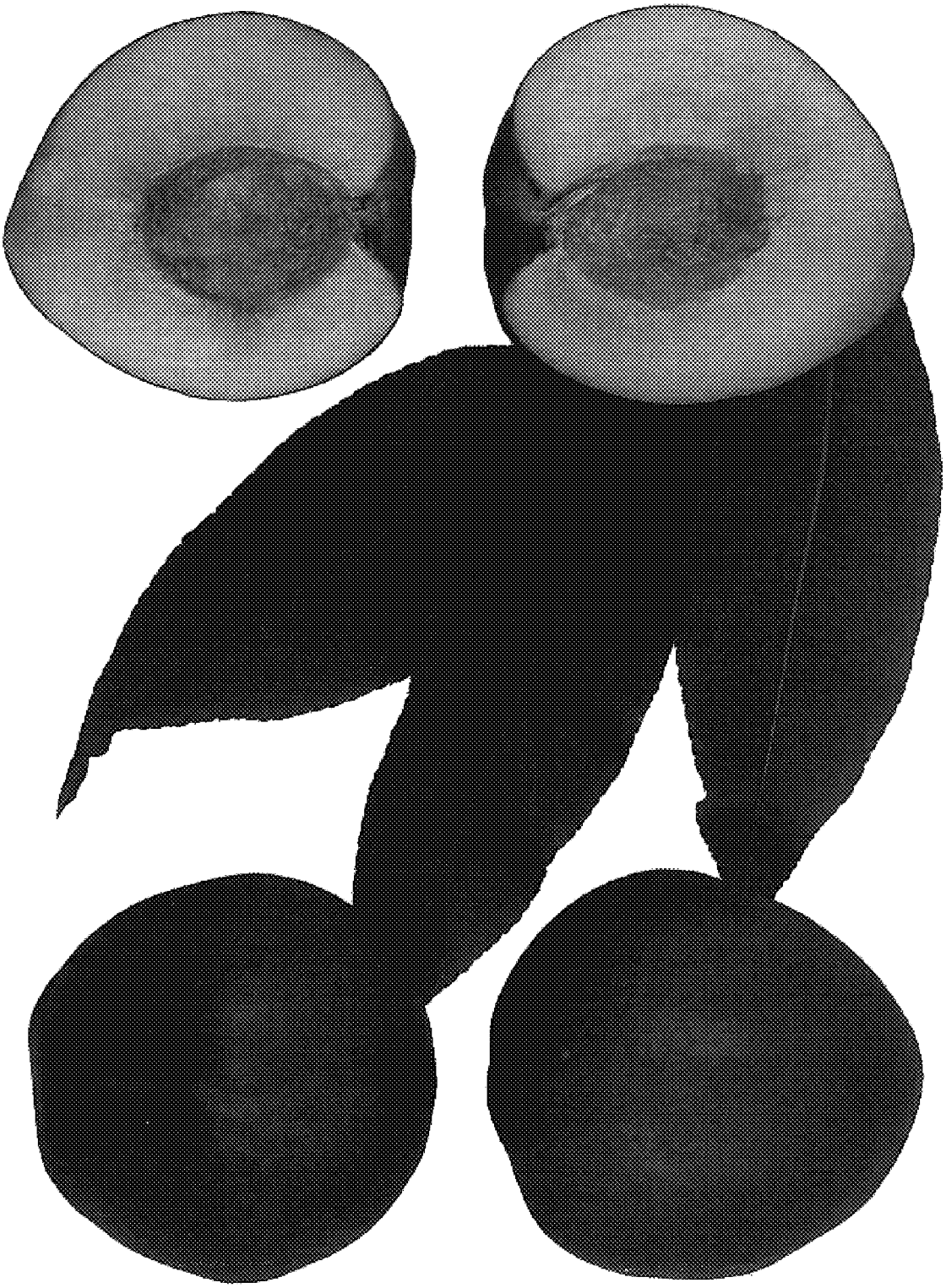

* * * * *